United States Patent [19]
Lee

[11] Patent Number: 5,268,568
[45] Date of Patent: Dec. 7, 1993

[54] MARKER DYE BAND DETECTOR FOR GEL ELECTROPHORESIS USING BALANCED LIGHT EMITTERS

[76] Inventor: Thomas E. Lee, 1306 E. 54th St. Apt. 2, Chicago, Ill. 60615

[21] Appl. No.: 983,644

[22] Filed: Nov. 30, 1992

[51] Int. Cl.$^5$ ............................................. H01J 40/14
[52] U.S. Cl. .................. 250/214 B; 250/573; 356/344
[58] Field of Search .................. 250/458.1, 461.2, 573, 250/214 B, 214 A; 204/182.8, 180.1, 299 R; 356/344

[56] References Cited

U.S. PATENT DOCUMENTS

| | | | |
|---|---|---|---|
| 4,534,647 | 8/1985 | Gross et al. | 356/344 |
| 5,120,419 | 6/1992 | Papp | 204/299 |
| 5,213,673 | 5/1993 | Fujimiya et al. | 204/299 R |

OTHER PUBLICATIONS

Paul et al., "A Simple Optoelectronic Device for Controlling an Electrophoresis Apparatus", Univ. of Florida, May 1989.

Primary Examiner—David C. Nelms
Assistant Examiner—K. Shami

[57] ABSTRACT

A device for detecting the marker dye band which is used to monitor the progression of biological macromolecules in gel electrophoresis. This device mounts external to the gel box, and utilizes a single light detector and a pair of AC activated light sources. The light sources produce reflected or transmitted light signals which, when balanced at the detector, cancel. When marker dye is absent the light signals are balanced, and no signal is detected. When marker dye is present at a specific detection point within the gel, the light reflected (or transmitted) is no longer balanced and a signal is detected.

11 Claims, 3 Drawing Sheets

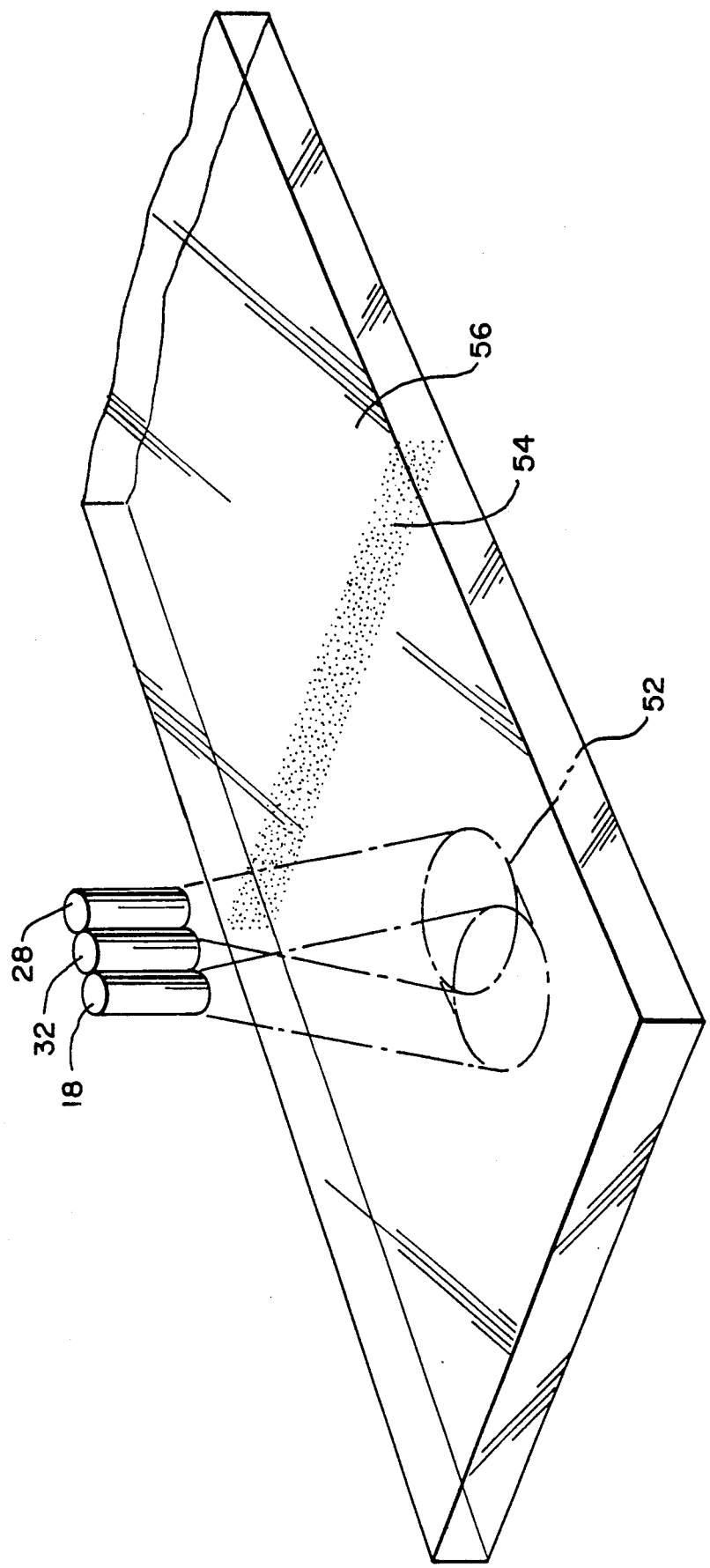

MARKER DYE BAND DETECTOR FOR GEL ELECTROPHORESIS USING BALANCED LIGHT EMITTERS

BACKGROUND

1. Field of Invention

This invention relates to detection of a marker dye band which is used to monitor the progression of biological macromolecules in gel electrophoresis.

2. Description of Prior Art

Probably the most powerful tool to study biological macromolecules such as DNA, RNA and proteins, is gel electrophoresis. Gel electrophoresis separates charged molecules on the basis of size and charge. (see Molecular Cloning 2nd edition Sabrook, Fritsch, Maniatis Cold Spring Harbor Laboratory Press 1989.) The progress of molecules through the gel is generally monitored by eye, by following the progress of marker dyes such as bromophenol blue or xylene cyanol FF. When the migration of the marker dye approaches the end of the gel, the voltage is turned off and the gel is analyzed.

Since the migration of molecules through the gel often times requires hours, an apparatus which can detect the marker dye as it approaches the end of the gel would be a great aid. Such a device would allow a gel to be run unattended, for example overnight, prevent over running a gel, and would allow marker dyes to always run the full length of the gel, thus obtaining the greatest resolution.

OBJECTS AND ADVANTAGES

Accordingly we claim the following as our objects and advantages of the invention: to provide a detection apparatus which is able to detect the marker dye used in gel electrophoresis when the marker dye has reached a specific spot in the gel, for example the end of the gel, and to produce an electrical signal which could be used, for example, to actuate an alarm or control a power source.

BRIEF DESCRIPTION OF THE DRAWINGS

FIG. 3—Orientation of optical elements in relation to a gel in the preferred embodiment.

LIST OF OBJECTS IN FIGURES

Figure 1:
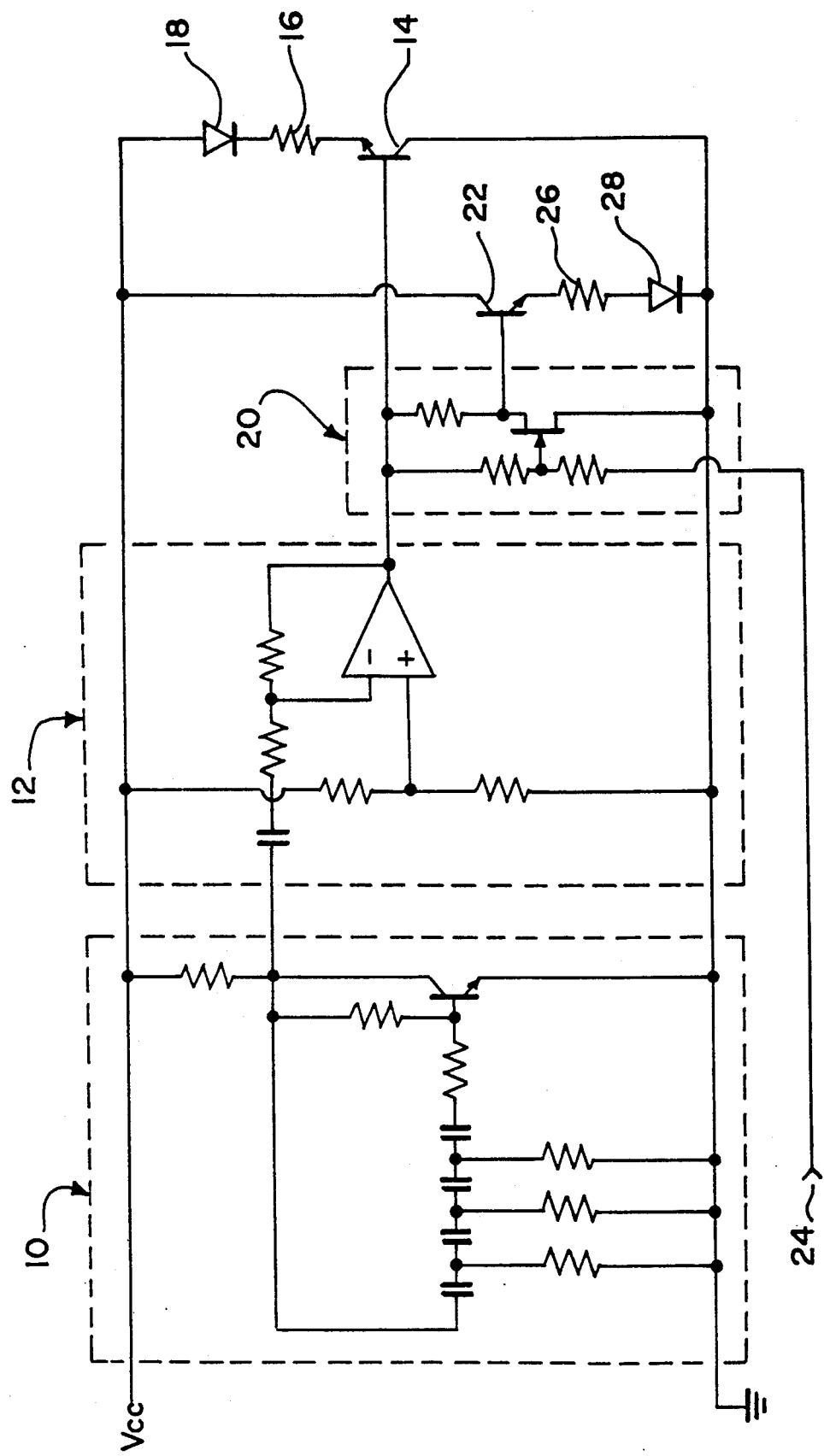
FIG. 1—Circuit diagram of transmitter for preferred embodiment

10. Oscillator
12. Amplifier circuitry to buffer oscillator 10
14. driver transistor for LED 18
16. driver resistor for LED 18
18. LED
20. Active voltage divider circuitry
22. Driver transistor for LED
24. Voltage input point to control active resistor divider circuitry 20
26. Driver resistor for LED 28
28. LED
32. Photo transistor
34. OpAmp which amplifies signal from Photo transistor 32
36. Parallel resistor and capacitor
38. Negative feed back circuitry
39. Voltage reference circuitry
40. Band pass amplifier
42. Peak detection circuitry.
43. Output
44. Voltage divider
52. Detection point
54. Marker dye band
56. Gel

DESCRIPTION OF THE PREFERRED EMBODIMENTS

Figure 2:
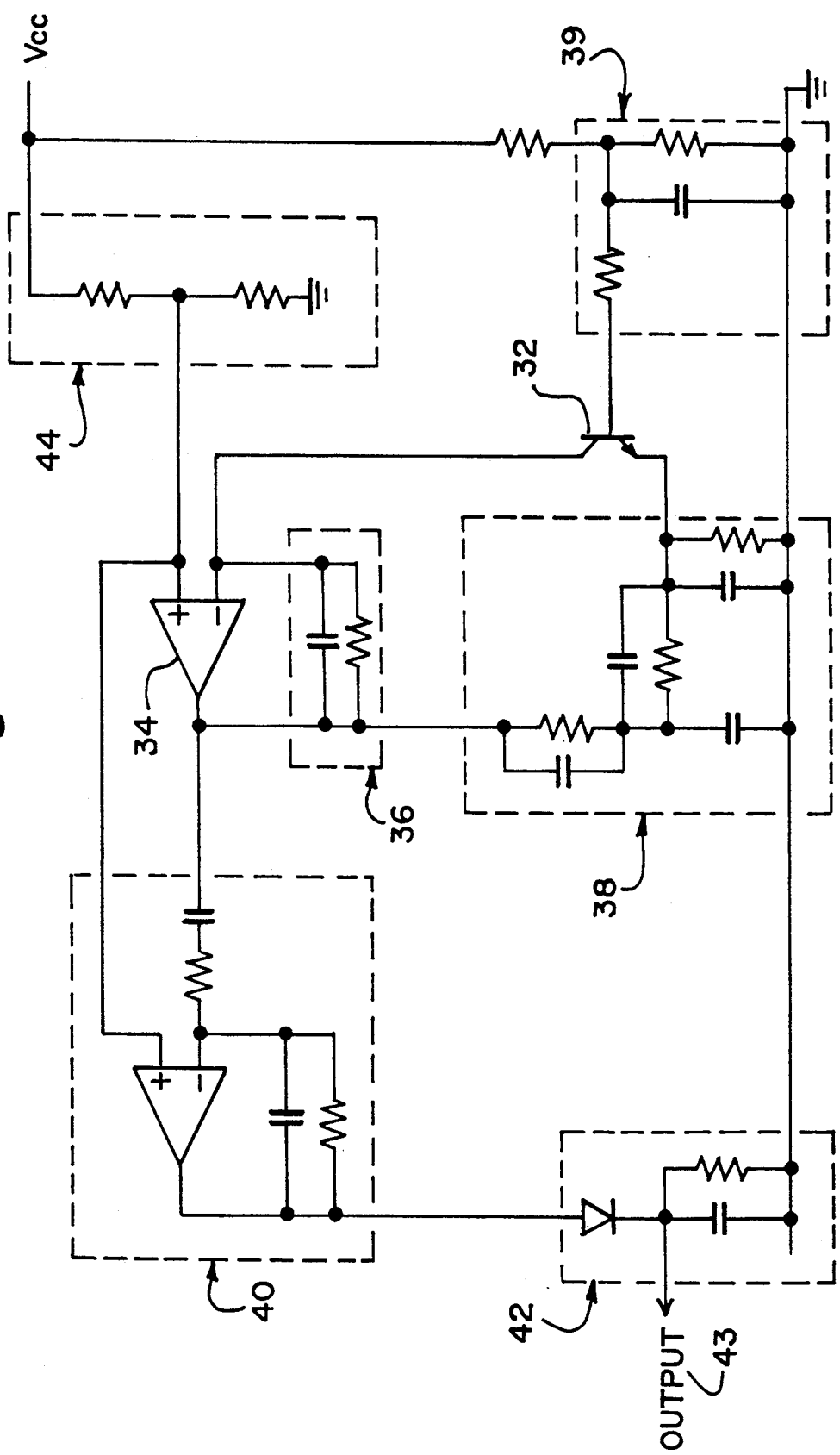
FIG. 2—Circuit diagram of receiver for preferred embodiment

A circuit diagram for the preferred embodiment is shown in FIGS. 1 and 2. The transmitter is shown in FIG. 1 and the receiver is shown in FIG. 2. The transmitter includes the oscillator 10 which generates a sine wave with a high enough frequency to be easily distinguishable from ambient light sources. This sine wave is buffered and given the correct D.C. level through amplifier circuitry 12. Amplifier circuitry 12 directly drives transistor 14 which is in an emitter follower configuration. Transistor 14 and resistor 16 sink a sinusoidally varying current with a D.C. component from LED 18 such that the LED is always emitting light but light intensity will vary sinusoidally. Amplifier circuitry 12 also delivers the sine wave to active voltage divider circuitry 20 which drives transistor 22. Active voltage divider circuitry 20 allows the amplitude of the sine wave which drives transistor 22 to be controlled by an externally applied D.C. voltage designated "the balance voltage" which is applied at input 24. Transistor 22 and resistor 26 source a sinusoidally varying current with a D.C. component to LED 28 such that LED 28 is always emitting light but light intensity will vary sinusoidally. LED 28 and LED 18 produce, therefore, sinusoidally varying light signals which are 180 degrees out of phase with one another. Values for resistors 26 and 16 are chosen such that the amplitude of the sinusoidal light signal coming from LED 28 can be varied through a sufficient range so as to balance the sinusoidally varying component of the light signals coming from LED 28 and LED 18 as described below in the OPERATION section.

In the receiver, which is shown in FIG. 2, the signal from photo transistor 32 is amplified through OpAmp 34. The parallel resistor and capacitor 36 are chosen such that OpAmp 34 does not amplify signals lower than the frequency of the sine wave produced by the oscillator 10. Negative feed back circuitry 38 provides negative feed back of signals, such as those produced by ambient light, which are below or above the frequency produced by the oscillator 10. Voltage reference circuitry 39 provides a voltage reference at high impedance to the base of the photo transistor 32 for the correct operation of negative feedback circuitry 38. The signal produced from OpAmp 34 is further filtered and amplified through band pass amplifier 40. The peak signal from band pass amplifier 40 is detected by peak detection circuitry 42. When no signal is present of the correct frequency, peak detection circuitry 42 produces a D.C. voltage which is determined by voltage divider 44. When a signal is present of the correct frequency, peak detection circuitry 42 produces a D.C. voltage more positive than voltage divider 44. The signal from peak detection circuitry 42 can be tested at output 43.

The orientation of LED 18, LED 28 and photo transistor 32 are shown in FIG. 3. LED 18 and LED 28 and photo transistor are positioned atop the gel box, and are aligned along the axis of migration through the gel.

Photo transistor 32 is located between LED 18 and LED 28, and aimed to receive light for LED 18 and LED 28 which is reflected back from the gel at approximate detection point 52.

OPERATION

The underlying principle by which this devices operates is that the two LEDs produce signals which, when balanced, cancel. In operation, the signals from the LEDs are adjusted so that they balance while the marker dye band is not at detection point 52 in the gel. When the marker dye band migrates to detection point 52 in the gel, the change of color in the gel, changes the relative amount of light from LED 18 and LED 28 reflected back from detection point 52. Thus, the signals are no longer balanced.

Therefore, in order to detect the marker dye band, the balance voltage must be adjusted before the band has migrated to the detection point 52. The balance voltage is adjusted so that the sine wave signals from LED 28 and LED 18, which are reflected back to the position of the photo transistor 32, cancel. The sine waves, which are 180 degrees out of phase with one another, can cancel when their amplitudes are the same. When the light signals from the two LEDs cancel, the photo transistor 32, OpAmp 34, and band pass amplifier 40 will have no signal of the proper frequency to amplify and detection circuitry 42 will produce the voltage determined by voltage divider 44.

When the marker dye band has migrated to the detection point, the change in color at point 52 reflects light to the photo transistor from one LED to a greater extent than light from the other LED. The sine waves are no longer balanced and therefore they do not cancel. The photo transistor 32, therefore detects a sine wave component from the LEDs, which is amplified by OpAmp 34 and Band pass amplifier 40 to produce a positive voltage from detection circuitry 42, which is larger than the voltage of voltage divider 44.

The change in the relative amount of light received by photo transistor 32 from LED 18 and 28 can take place by several mechanisms. One mechanism would require that LED 18 and 28 be of different color such that the colored marker dye, when present at position 52, will reflect light from the two LEDs by different magnitudes. A second mechanism would require that the two LEDs are aimed at slightly different locations on the gel such that as the marker dye approaches point 52 it will begin effecting the light from one LED before it begins effecting the light from the other LED.

LED 18 and 28 and photo transistor 32 need not be located on the top of the gel. All three could be located below the gel (since most gel boxes are transparent); or LED 18 and 28 could be located on the opposite side of the gel from photo transistor 32, and could operate by transmitting through the gel. If LED 18 and 28, and photo transistor 32 are located on the top of the gel box, some method such as a small heating element might be provided to prevent condensation on the lid of the gel box.

These alternating light intensities emitted by LED 18 and 28 need not be restricted to sinusoidal wave forms. Any set of wave forms f(t) and g(t) will work provided that there is some constant K where $f(t)+K*g(t)=C$ where C is a constant with respect to time, and there is some receiver which can distinguish f(t) and g(t) from ambient light. For example square waves which are 180 degrees out of phase can also be made to cancel, and the detection circuitry could include a commutating filter to pass this complex wave form.

SUMMARY

Thus the reader can see that the marker dye detector of the invention provides a highly sensitive detection scheme which is insensitive to ambient light, yet even a small imbalance between the two light sources can easily be detected by the tuned receiver. This method requires no materials with critical or special optical properties, or critical construction angles. Thus, the invention provides a reliable method for the detection of a marker dye band in gel electrophoresis, and can therefore allow increased automation in gel electrophoresis.

What is claimed is:

1. An electro-optical marker dye band detector for gel electrophoresis, capable of detecting the presence or absence of a visible marker dye band when said marker dye band has migrated to a specific detection point in the gel, comprising:
    a) two light emitting elements,
    b) a light detecting element,
    c) a means for energizing said light emitting elements such that one emits light which varies in intensity according to a function f(t), and the other emits light which varies in intensity according to a function g(t), where said functions f(t) and g(t) satisfy the condition that there is some constant k and some constant c such that $f(t)+k*g(t)=c$,
    d) a means of amplifying the signal from said light detecting element such that signals of the form f(t) and g(t) are amplified but not signals from ambient light sources,
    e) said light emitting elements and said light detecting element are so positioned that the migration of said marker dye band to said detection point will cause a change in the relative amount of light from said two light emitting elements reaching said light detecting element which is detectable by said amplifying means,
    f) some means for adjusting the amplitude of said function g(t) so that the condition $f(t)+k*g(t)=c$ is fulfilled at the position of the photo detecting element before said visible marker dye band has migrated to said detection point within said gel.

2. The marker dye detector of claim 1 wherein said light emitting elements and said light detecting element are located on the same side of said gel.

3. The marker dye band detector of claim 2 wherein a heating element is used to prevent condensation on the inside of gel container where condensation might effect the operation of said marker dye detector.

4. The marker dye detector of claim 1 wherein said light emitting elements are located on the opposite side of said gel from said light detecting element, and light is detected after it passes through said gel.

5. The marker dye detector of claim 1 wherein said light detecting elements emit light of different color such that a change in color of said gel due to the presence of said marker dye band causes a change in the relative amount of light received by said light detecting element.

6. The marker dye detector of claim 1 wherein said function f(t) is a sine wave and said function g(t) is a sine wave 180 degrees out of phase with function f(t).

7. The marker dye detector of claim 1 wherein said function f(t) is a square wave and said function g(t) is a square wave 180 degrees out of phase with function f(t).

8. The marker dye detector of claim 1 wherein said function f(t) is a triangle wave and said function g(t) is a triangle wave 180 degrees out of phase with function f(t).

9. The marker dye detector of claim 1 wherein said light emitting elements are LEDs.

10. The marker dye detector of claim 1 wherein said light detecting element is a photo transistor.

11. The marker dye detector of claim 1 wherein said light emitting elements and said light detecting element are positioned in line along the migration path of said marker dye band through said gel such that said light detecting element is located between said light emitting elements.

* * * * *